United States Patent [19]
Kristensen et al.

[11] Patent Number: 5,836,015
[45] Date of Patent: Nov. 17, 1998

[54] PANTS WITH HIP PROTECTORS

[75] Inventors: Johannes Nyvang Kristensen, Ikast; Finn Kjærgaard, Viborg, both of Denmark

[73] Assignee: Tytex A/S, Ikast, Denmark

[21] Appl. No.: 849,856

[22] PCT Filed: Jan. 5, 1995

[86] PCT No.: PCT/DK95/00006

§ 371 Date: Jun. 12, 1997

§ 102(e) Date: Jun. 12, 1997

[87] PCT Pub. No.: WO96/20615

PCT Pub. Date: Jul. 11, 1996

[51] Int. Cl.⁶ .................................................. A41D 13/00
[52] U.S. Cl. .......................... 2/23; 2/455; 2/228; 2/69
[58] Field of Search .............................. 2/23, 69, 22, 79, 2/227, 228, 238, 455, 456

[56] References Cited

U.S. PATENT DOCUMENTS

| | | | |
|---|---|---|---|
| 759,833 | 5/1904 | Stall | 2/228 |
| 4,894,867 | 1/1990 | Ceravolo et al. | 2/228 |
| 4,987,613 | 1/1991 | Loverdi et al. | 2/23 |
| 5,050,244 | 9/1991 | Kleinman | 2/227 |
| 5,052,052 | 10/1991 | Gilford et al. | 2/23 |
| 5,105,473 | 4/1992 | Valtakari | 2/227 |
| 5,134,726 | 8/1992 | Ross | 2/227 |
| 5,161,257 | 11/1992 | Arensdorf et al. | |
| 5,361,410 | 11/1994 | Sigl | 2/23 |
| 5,497,511 | 3/1996 | Zade | 2/238 |
| 5,551,082 | 9/1996 | Stewart et al. | 2/228 |
| 5,572,737 | 11/1996 | Valice | 2/22 |
| 5,689,836 | 11/1997 | Fee et al. | 2/22 |
| 5,706,523 | 1/1998 | Witzel | 2/238 |

FOREIGN PATENT DOCUMENTS

| | | |
|---|---|---|
| 0643929 | 3/1995 | European Pat. Off. |
| 2152284 | 4/1973 | France. |
| 8603019 U | 5/1986 | Germany. |

*Primary Examiner*—Gloria M. Hale
*Attorney, Agent, or Firm*—Watson Cole Grindle Watson, P.L.L.C.

[57] ABSTRACT

Flexible hip protectors (1) of an approximately domed shape are located and fixed in positions confronting the neck of either femur in so-called usual pants (21) so as to cover corresponding portions of the necks of the femurs. Therefore, if a person wears the pants (21), the hip protectors (1) are always located at exact positions so as to protect the necks of the femurs. Accordingly, the pants (2) with the protectors (1) are effective for wearing the protectors (1).

7 Claims, 7 Drawing Sheets

PANTS WITH HIP PROTECTORS

FIELD OF THE INVENTION

This invention relates to pants having protectors in order to decrease the occurrence ratio of injuries such as bone fractures of a neck of a femur due to falling.

BRIEF DESCRIPTION OF THE PRIOR ART

Elderly or physically debilitated persons easily fall down even in usual walking and often suffer a fracture or the like. However, there have been effective measures to prevent such incidents heretofore. Therefore, a hip protector for protecting the neck of a femur from the outside has recently been developed. This hip protector is formed into an approximately domed shape so as to cover a portion corresponding to the neck of the femur and is available for not only elderly persons but also sportsmen.

However, means for easy installation of the above newly developed protector at a specific position have not yet been developed. Since the above protector is formed into an approximately domed shape, the protector must be fixed exactly to cover a portion corresponding to the neck of the femur in order to protect the neck of the femur by employing this hip protector. It is generally suggested that the protector should be fixed by means of a belt. For example, the protector can be fixed by winding a belt around the hip and connecting the belt to an end of the hip protector with a band or the like as in a gun belt while winding another belt around the thigh to fix the other end of the protector. However, it is difficult for a person to walk with such a belt on one's thigh and also to put on or take off the belt.

Besides, it is proposed to attach the hip protector removably on a reverse side of trousers or the like. For example, there is a method of installing magic tape on both of the hip protectors and the reverse side of trousers, or a method of installing a removable adhesive agent only on the hip protector. However, the former method has drawbacks related to the trouble of installing magic tape in all trousers at hand and also related to difficulties in fixing surely on a portion corresponding to the neck of the femur because trousers are usually loose-fitting. On the other hand, the latter method has the drawback that an adhesive agent itself cannot work with repeated use.

U.S. Pat. No. 5,134,726 discloses a pair of sports pants with protective hip pads arranged in pockets at the hip areas. It is disclosed to use flexible pads for a protection of a person during sports activities. Even though the hip pads would give protection in some situations then it would not give sufficient protection to protect a fragile neck of a femur of elderly debilitated persons.

OBJECT OF THE INVENTION

Accordingly it is an object of the present invention to provide pants with protectors which do not become a nuisance when walking, which are easy to put on and take off, and which can protect the neck of the femur.

DISCLOSURE OF THE INVENTION

To accomplish the above object, pants with hip protectors according to this invention have a belly portion, a buttock portion and a crotch portion positioned between openings for both legs, each of the hip protectors being formed into an approximately domed shape so as to cover a portion corresponding to a neck of a femur, each of said hip protectors being flexible, each of the hip protectors being located in a pocket means at positions corresponding to the neck of the femur on both sides of right and left when the pants are being worn, and that the hip protectors have flexibility with the following flat compressive strength (A) and lateral compressive strength (B):

(A) a flat withstand load in 10 mm displacement of 196 to 980N (20 to 100 kgf), (B) a lateral withstand load in 10 mm displacement of 49 to 294N (5 to 30 kgf).

Thus, hip protectors are positioned and fixed in pants according to the invention so as to confront the neck of the femur on both sides of the body when the pants are being worn. Therefore, if a person wears the pants with protectors, each hip protector is located at a portion so as to confront the neck of the femur. In detail, if a person puts on the pants with protectors, the hip protectors can always be situated on exact positions so as to protect the necks of the femurs without trouble in locating the necks of the femurs and arranging the hip protectors on portions corresponding thereto whenever a person uses the hip protectors.

The above hip protector is formed into an approximately domed shape so as to cover a portion corresponding to the neck of the femur. As a result, when a person wears the pants with protectors, a cavity is formed between a portion corresponding to the neck of the femur and the hip protector formed into an approximately domed shape. Therefore, if a person wearing the pants falls, the protector is deformed elastically and becomes flatter with an impact with falling (resulting in a smaller cavity) so as to absorb the impact, which decreases the occurrence ratio of a bone fracture and the like of the neck of the femur.

The pants with protectors according to the invention comprise so-called usual pants having a belly portion, a buttock portion and a crotch portion positioned between openings for both legs and hip protectors fixed therein. For this reason, a person can obtain a comfortable fit when wearing the pants with protectors without tightening the body with belts and the like in the same condition as when wearing usual pants except for a portion installed with hip protectors.

According to the specific embodiment, the pants should have three layers of fabric in the area of each pocket means. This is the case when the pants are tailored and when actual pockets are provided having a covering sheet which ensures that the hip protector does not fall out of the pocket. Moreover, the three layers would enhance the protective effect by giving a better shock absorbing effect.

According to a further embodiment, the pants have legs in such a way that the leg openings are provided beneath the crotch portion. Hereby it is ensured that the pants have a sufficient area for including the pocket means in front of the neck of the femur. In this embodiment the pants may be tailored or be manufactured by knitting or crocheting.

According to a further embodiment, the pants are manufactured in such a way that they are elastically contractible and exert a pressure against the user or the total extension. This embodiment is especially half-knitted or circular knitted in which the elastic contractibility is obtained by the knitting pattern or by knitting in elastic yarns. In this situation, the pants will exert a pressure against the user, however, having less pressure in the area of the pocket means. Hereby the hip protector would be arranged in the looser area, which is surrounded by the stronger and more elastic contractible hip protector area.

However, even in the area of the pocket means there would be an elastic contractibility in order to maintain the hip protector in a correct position corresponding to the neck of the femur.

Next, referring to the drawings, the present invention is described in detail with embodiments.

Figure 3:
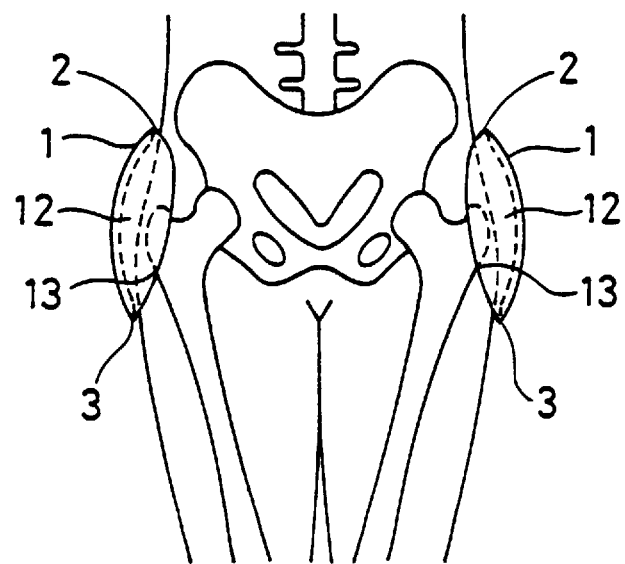
Figure 4:
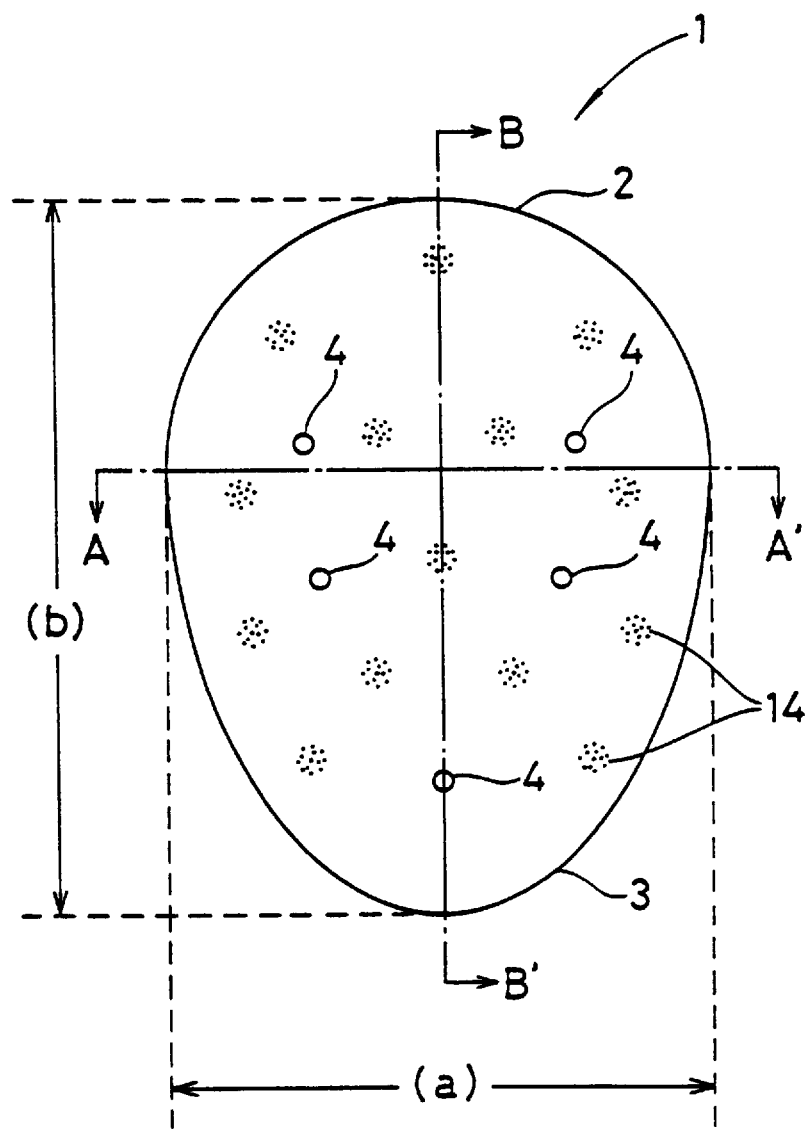
Figure 5:
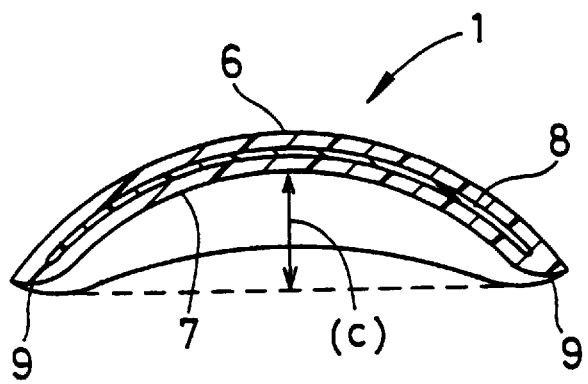
Figure 6:
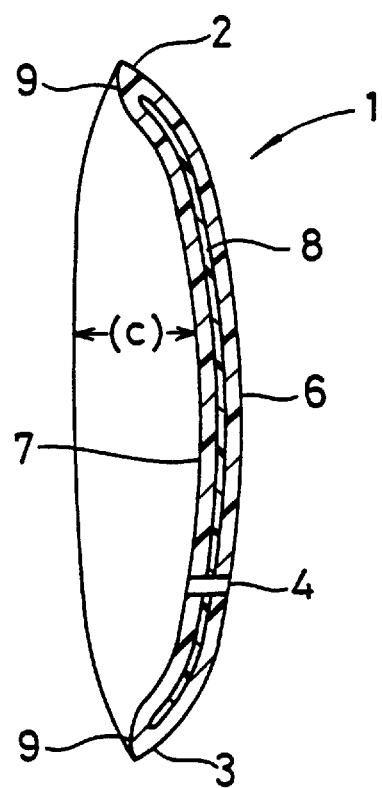
Figure 7:
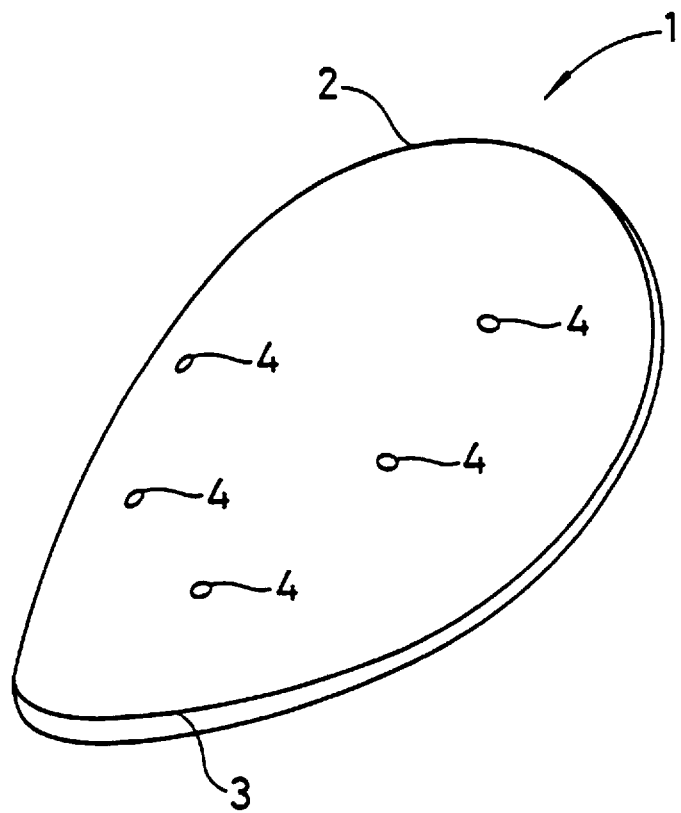
Figure 8:
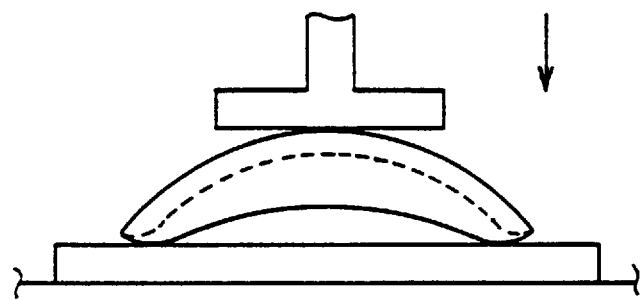
Figure 9:
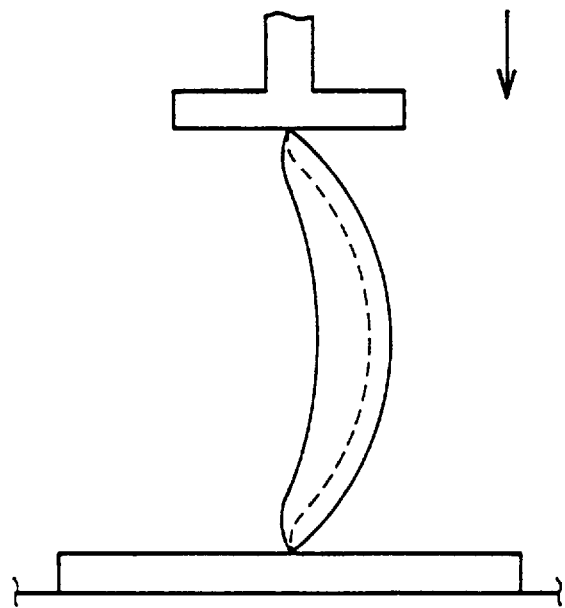
Figure 10:
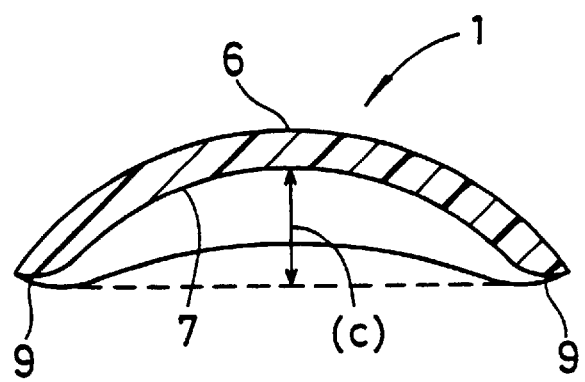
Figure 11:
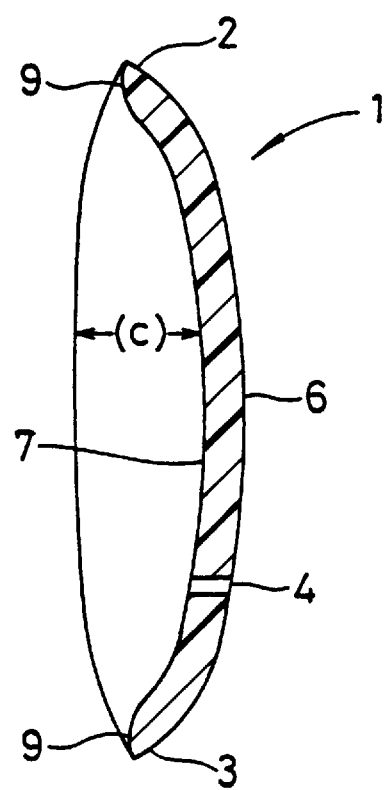

FIG. 3 is a typical front view illustrating positions where the hip protectors of the above embodiment are located, FIG. 4 is a front view of one embodiment of a hip protector employed in the above embodiment, FIG. 5 is a cross-sectional view taken along line A-A' of FIG. 4, FIG. 6 is a longitudinal sectional view taken along line B-B' of FIG. 4, FIG. 7 is a perspective view of the hip protector in FIG. 4 seen slantwise from above, FIG. 8 illustrates a typical way of measuring the flat compressive strength (A) of the hip protector, FIG. 9 illustrates a typical way of measuring the lateral compressive strength (B) of the hip protector, FIG. 10 is a cross-section view of another embodiment of the hip protector, and FIG. 11 is a longitudinal sectional view of another embodiment.

The following example is further illustrative of the invention.

EXAMPLE 1

Figure 1:
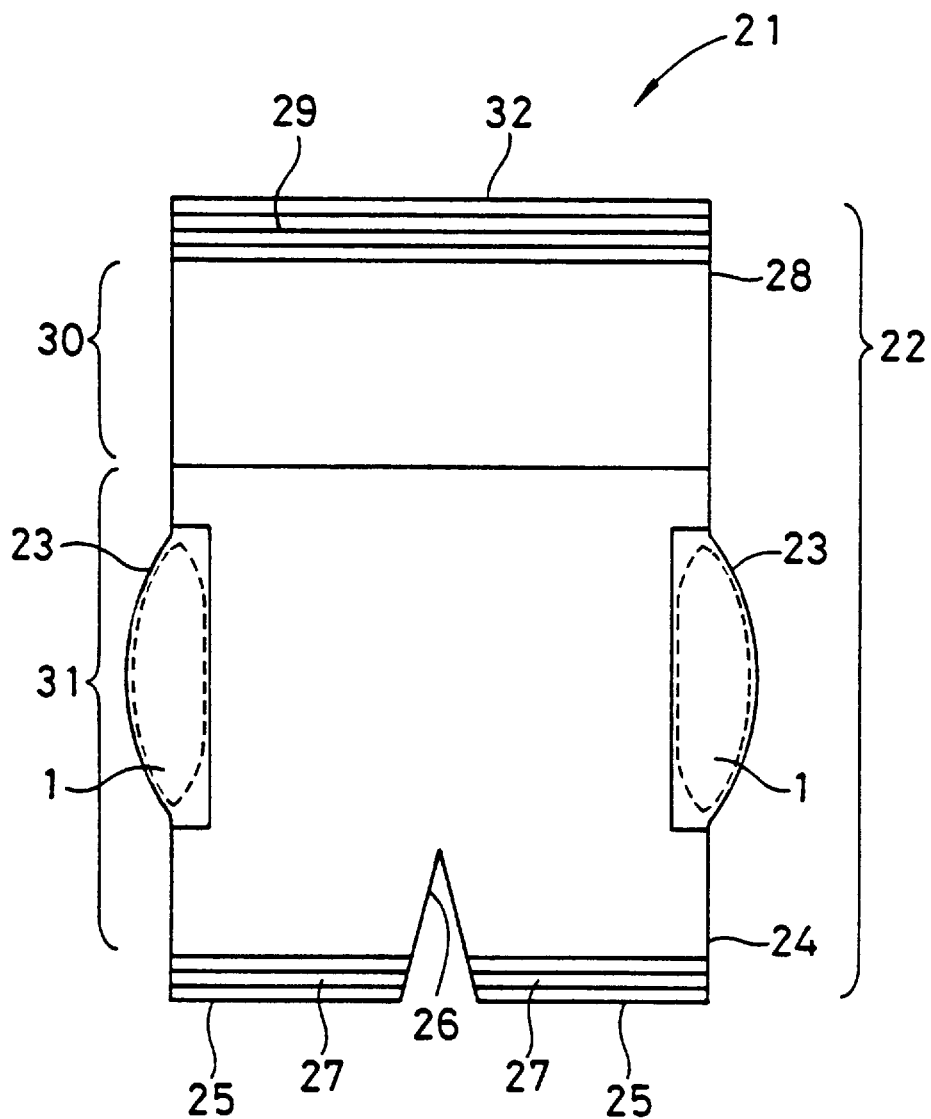
FIG. 1 is a front view of one embodiment of the present invention.
Figure 2:
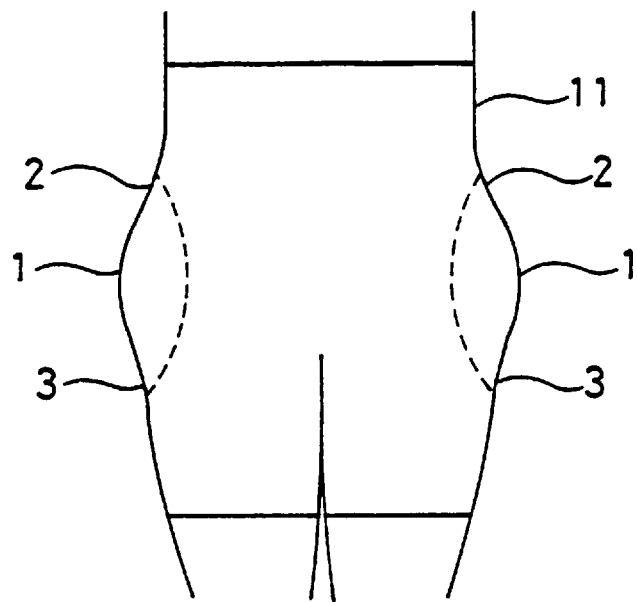
FIG. 2 is a front view in a state where the above embodiment is worn.

FIG. 1 is a front view of one embodiment of pants 21 with protectors according to the present invention, FIG. 2 is a front view in a state where pants 21 with protectors in the above embodiment are worn, and FIG. 3 is a typical front view illustrating positions where the hip protectors 1 of the above embodiment are located. In FIG. 1, the pants 21 with protectors 1 comprise a cylindrical body part 22 which is circular-knitted, pocket means 23 for fixing the hip protectors 1 therein, and hip protectors 1 housed and fixed in the pocket means 23, the total weight being 150 g. The two openings 25 for legs are arranged at lower end 24 of the cylindrical body part 22, and the crotch portion 26 is positioned between the two openings 25.

The pocket means 23 for fixing the hip protectors 1 are arranged on both right and left sides of the cylindrical body part 22 and are positioned so as to cover the corresponding parts of the neck of the femurs when wearing the pants 21 with hip protectors 1. The hip protectors 1 are contained in the pocket means 23 whose peripheries are seamed. Each hip protector 1 in an approximately domed shape in order to cover the part corresponding to the neck of a femur is formed into an ellipse in a plan view and is contained in a state where the major axis of the ellipse is arranged perpendicularly and a concave side is attached to a body.

In the cylindrical body part 22, an upper part 30 is knitted so that flexibility is increased gradually toward an upper end 28 while a lower part 31 is knitted so that flexibility is increased gradually toward a lower end 24. The crotch portion 26 is formed by steps comprising circular-knitting the cylindrical part 22, cutting a center of the lower end 24, and seaming front left side leg and back left side leg, front right side leg and back right side leg respectively.

Leg bands 27 and a waist band 29 are arranged on the openings for legs 25 and the upper end 28 of the cylindrical body part 22 respectively. The waist band 29 is knitted with a rib stitch 32 without turn-up while the leg bands 27 are knitted in the same way as the waist band 29. However, the flexibility of the leg bands 27 is smaller than that of the waist band 29.

Now the hip protectors 1 are described in detail.

FIG. 4 is a front view of one embodiment of an approximately dome-shaped hip protector 1 employed in the present invention with a convex side of the hip protector 1 up and a concave side thereof down. FIG. 5 is a cross-sectional view taken along line A—A' of FIG. 1, FIG. 6 is a longitudinal sectional view taken along line B—B' of FIG. 1, and FIG. 7 is a perspective view of the hip protector 1 in FIG. 4 seen slantwise from above. In FIG. 4, the hip protector 1 is shaped into an oblong in a plan view whose lower part 3 terminates in a comparatively more acute end than the upper part 2, wherein the minor axis (a) is 11.5 cm while the major axis (b) is 16 cm.

This hip protector 1 comprises polypropylene foam wherein a reinforcing core 8 made of a hard polypropylene plate member is embedded. The reinforcing core 8 is approximately the same shape as that of the hip protector 1 and is embedded in almost all of the hip protector 1. That is, the size of the reinforcing core 8 is smaller than that of the hip protector 1 so that the reinforcing core 8 does not appear at the surface of the hip protector 1. In FIGS. 5 and 6, the reinforcing core 8 is 2 mm in thickness. Furthermore, a flat withstand load (A) is about 294N (30 kgf) in 10 mm displacement, a lateral withstand load (B) is about 98N (10 kgf) in 10 mm displacement and a shock absorbing ability is 25%.

In the hip protector 1, five vent holes 4 for perspiration with a 0.5 cm diameter are formed so as to pass through from the front side to the reverse side. Furthermore, a plurality of anti-slipping areas 14 is established on the convex side 6 of the hip protector 1 at specific intervals. Similar anti-slipping areas 14 are also established on the concave side 7.

The thickness of the protector is 0.85 cm and the depth (c) of the dome is 2 cm. A marginal area of the concave side 7 of the dome is chamferred and formed into a rounded rim 9 so as to slide in bending with an impact on the hip protector 1 and not to prevent such a bending.

As mentioned above, the hip protector 1 is formed into an approximately domed shape wherein the rounded rim 9 is established in the marginal area of the concave side 7 and the marginal area of the convex side 6 is flexible so that a cavity 12 (in FIG. 3) is formed between the body and the center part of the concave side 7 when the hip protector 1 is applied on the part corresponding to the neck of the femur with concave side 7 inside. In such a state, if the person falls, an impact is imparted to the hip protector 1 and the compression power is added to the domed shape, the domed shape becomes flatter (resulting in smaller cavity 12) to absorb the impact (shock absorbing ratio: 25%).

The hip protector 1 comprises polypropylene foam wherein the reinforcing core 8 made of a hard polypropylene plate member is embedded. Thanks to the material and the approximately domed shape, a flat withstand load (A) in 10 mm displacement becomes 294N (30 kgf) while a lateral withstand load (B) in 10 mm displacement becomes 98N (10 kgf). For this reason, the hip protector 1 can fully endure such an impact. Since the hip protector 1 and the reinforcing core 8 are composed of relatively lightweight polypropylene foam having strength, heat resistance and water resistance, the hip protector 1 itself becomes lightweight and can be safely laundered without damages or deformation or the like in a state where it is fixed inside the pants 21. Moreover, pants 21 with protectors 1 are made so as to endure boil washing due to their sufficient heat resistance.

Since vent holes 4 for perspiration are established in the hip protector 1, the user can wear the hip protector 1 comfortably without feeling stuffiness in the relative part. Especially, it demonstrates its effect when the user becomes sweaty like in the summer or while playing sports. Furthermore, since a plurality of anti-slipping areas 14 are established at specific intervals on the convex side 6 and similar anti-slipping areas 14 are established on the concave side 7, the hip protector 1 can be fixed without sliding, resulting in a comfortable feeling for the user.

A method of measuring the above compression strength is described here. Both flat compressive strength (A) and lateral compressive strength (B) are measured with a compression jig by Instron universal tester. The values measured by compression with a head speed of 1 mm/minute in each direction shown in FIGS. 8 and 9 are obtained as the flat compressive strength (A) and the lateral compressive strength (B) respectively.

Besides, a method of measuring the shock absorbing ratio is described here. An apparatus and conditions are shown as follows.

Apparatus: A graphic impact tester made by Toyoseiki
A falling body: 13 mm in diameter
Fall height: 0.4 m
A weight's weight: 6.5 kg The values are indicated in the load cell of the above apparatus as all absorbing energy (J). In addition, the formula for obtaining the shock absorbing ratio is shown below.

$$\frac{\text{all absorbing energy } (J = kgm^2s^{-2})}{\text{a weight's weight (kg)} \times \text{gravitational acceleration (ms}^{-2}) \times \text{fall height (m)}} = \text{shock absorbing ratio (\%)}$$

The all absorbing energy is 6.37 J joule) in example 1 under the above conditions. Therefore, the shock absorbing ratio of 25% is derived by the above formula.

In this way, the hip protector 1 is composed.

As mentioned above, since the pants 21 with protectors 1 according to the present invention comprise the cylindrical body 22, the pocket means 23 for fixing the protectors 1 therein and the hip protectors 1, the pants 21 with protectors 1 are comfortable to wear without obstruction for walking and without the tight feeling of a belt or the like. In addition, the pocket means 23 for the hip protectors 1 are established on both right and left sides of the cylindrical body part 22 so as to be positioned to cover the portions corresponding to the necks of the femurs when being worn. Therefore, it is no problem to identify the positions of the necks of the femurs and fix the hip protectors 1 on the positions confronting them whenever employing the hip protectors 1. That is, only if putting on the pants 21 with protectors 1, the protectors 1 can surely cover the portions corresponding to the necks of the femurs, which brings about a comfortable fit without sliding. Besides, since the cylindrical body part 22 is circular-knitted and flexibility is increased gradually toward the upper end 28 in the upper part 30 while flexibility is increased gradually toward the lower end 24 in the lower part 31, the pants 21 with protectors 1 to fit a body can be obtained easily without trouble in cutting.

Leg bands 27 and a waist band 29 are arranged on the openings for legs 25 and the upper end 28 of the cylindrical body part 22, respectively. The waist band 29 is knitted with a rib stitch 32 without turn-up while the leg bands 27 are knitted in the same way as the waist band 29. However, the flexibility of the leg bands 27 is smaller than that of the waist band 29. For this reason, suitable flexibility can be obtained in the upper end 28 of the cylindrical body 22, that is a waist part, and in openings 25 for legs without a loose fit and the like, which results in appropriate flexibility and heightened fitting feeling of the hip protectors 1.

The cylindrical body part 22 of the pants 21 with protectors 1 is composed of circular-knitting, which, however, is not to be construed in a limiting sense. The way of knitting such as in a rib stitch 32 on the waist band 29 of the cylindrical body part 22 or the leg bands 27 is not critical either. As another embodiment, the cylindrical body part 22 can be manufactured by steps comprising cutting a front side and a rear side separately, seeming them and attaching the pocket means 23 for fixing the hip protectors 1. Or various kinds of conventional pants can be adaptable by attaching the pocket means 23 for fixing the hip protectors 1 therein.

Furthermore, the size of the hip protector 1 in the above examples is not to be construed to limit the scope of the invention, however, it is preferable that a minor axis (a) is 9 to 14 cm, a major axis (b) is 13 to 18 cm, the thickness of the dome is 0.5 to 1.5 cm, a diameter of vent holes 4 is 0.2 to 0.7 cm and a depth (c) of the dome is 1.5 to 4.5 cm. Each optimum scope for a cavity between the portion corresponding to the neck of the femur 13 and the hip protector 1 is: 11.5 cm for a minor axis (a), 16 cm for a major axis, 0.85 cm for a dome thickness, 0.5 cm for a diameter of vent holes 4, and 2 cm for a dome depth (c), respectively. Especially, a diameter of the vent holes 4 is preferably not more than 0.7 cm to maintain the strength of the hip protector 1. Some care is necessary, though, and for example vent holes 4 are scattered.

As materials of the hip protector 1 and the reinforcing core 8, any material having a flat withstand load in 10 mm displacement of 196 to 980N (20 to 100 kgf) and a lateral withstand load in 10 mm displacement of 49 to 294N (5 to 30 kgf). and having a degree of flexibility like synthetic resin, and made of lightweight rubber and non-woven fabric except for steels, wood or the like is acceptable. The thickness of the reinforcing core 8 needs to be appropriately in accordance with the thickness of the dome of the hip protector 1 and preferably 1/10 to 1/3 of the dome's thickness.

Anti-slipping areas 14 to fix the hip protector 1 on pants 21 in the above example are not to be construed to limit the scope of the invention, and the number and the positions of the areas 14 can be varied appropriately according to material and the like of the pants.

As shown in FIGS. 10 and 11, the reinforcing core 8, such as a hard polypropylene plate member, may not be embedded inside the protector 1.

The hip protectors 1 are contained and fixed inside the pocket means 23 in the above example, however, the pocket means 23 may be provided with an opening for putting in and taking out the hip protector 1 so as to wear the pants 21 with or without the hip protector 1.

EFFECTS OF THE INVENTION

As mentioned above, hip protectors are positioned and fixed in pants according to the invention so as to confront the neck of the femur on both sides of the body when the pants are being worn. Therefore, if a person wears the pants with protectors, each hip protector is located at a portion so as to confront the neck of the femur. In detail, if a person puts on the pants with protectors, the hip protectors can always be situated on exact positions so as to protect the necks of the femurs without trouble in locating the necks of the femurs and arranging the hip protectors on portions corresponding thereto whenever a person uses the hip protectors.

The above hip protector is formed into an approximately domed shape so as to cover a portion corresponding to the neck of the femur. As a result. when a person wears the pants with protectors, a cavity is formed between a portion corresponding to the neck of the femur and the hip protector formed into an approximately domed shape. Therefore, if a person wearing the pants falls, the protector is deformed elastically and becomes flatter with an impact with falling (resulting in a smaller cavity) so as to absorb the impact, which decreases the occurrence ratio of a bone fracture and the like of the neck of the femur.

The pants with protectors according to the invention comprise so-called usual pants having a belly portion, a buttock portion and a crotch portion positioned between openings for both legs and hip protectors fixed therein. For this reason, a person can obtain a comfortable fit when wearing the pants with protectors without tightening the body with belts and the like in the same condition as when wearing usual pants except for a portion installed with hip protectors.

We claim:

1. Pants with hip protectors wherein said pants have a belly portion, a buttock portion and a crotch portion positioned between openings for both legs, wherein each of said hip protectors is flexible, each of said hip protectors is located in a pocket means on said pants at positions corresponding to the neck of the femur of each hip of said wearer when said pants are being worn, wherein each of said hip protectors is formed in an approximately domed shape so as to cover a portion corresponding to a neck of a wearer's femur, and wherein the hip protectors have flexibility with a flat compressive strength of (A) and lateral compressive strength of (B):

(A) a flat withstand load in 10 mm displacement of 196 to 980N (20 to 100 kgf), (B) a lateral withstand load in 10 mm displacement of 49 to 294N (5 to 30 kgf).

2. Pants with hip protectors according to claim 1 wherein said pants comprises a circular-knitted cylindrical body portion with said pocket means for said hip protectors.

3. Pants with hip protectors according to claim 1, wherein a total weight of said pants including hip protectors is set within 300 g.

4. Pants with hip protectors according to claim 1, including 3 layers of fabric in the area of each pocket means (23).

5. Pants with hip protectors according to claim 1, wherein said leg openings (25) are provided beneath the crotch portion (26) in that the pants comprise legs.

6. Pants with hip protectors according to claim 1, wherein the pants (21) are elastically contractible and exert a pressure against the user over the total extension.

7. Pants with hip protectors according to claim 1, wherein the pocket means comprises a loosely knitted area surrounded by a tightly knitted area which exerts a pressure against the wearer.

* * * * *